United States Patent [19]
Lai et al.

[11] Patent Number: 5,578,637
[45] Date of Patent: Nov. 26, 1996

[54] METHODS OF INHIBITION OR KILLING CANCER CELLS USING AN ENDOPEROXIDE

[75] Inventors: Henry C. Lai, Seattle; Narendra P. Singh, Lynnwood, both of Wash.

[73] Assignee: University of Washington, Seattle, Wash.

[21] Appl. No.: 434,452

[22] Filed: May 3, 1995

[51] Int. Cl.$^6$ .......................... A01N 43/16; A01N 43/02; A61K 31/35; A61K 31/335

[52] U.S. Cl. .......................... 514/450; 514/451; 514/452; 514/6; 514/23; 514/53; 514/54; 514/59

[58] Field of Search ..................... 514/450, 451, 514/452, 6, 23, 53, 54, 59

[56] References Cited

U.S. PATENT DOCUMENTS

| | | | |
|---|---|---|---|
| 4,978,676 | 12/1990 | Thornfeldt | 514/450 |
| 5,219,880 | 6/1993 | Thornfeldt | 514/450 |
| 5,225,427 | 7/1993 | Bindumadhavan et al. | 514/378 |

OTHER PUBLICATIONS

Sun et al., "Antitumor Activities of 4 Derivatives of Artemisic Acid and Artemisinin B in vitro," *Chung-Kuo-Yao-Li-Hsueh-Pao* 13:541–543 (1992).

Woerdenbag et al., "Cytotoxicity of Artimisinin–related Endoperoxides to Erlich Ascites Tumor Cells," *J. Nat. Prod.* 56(6):849–856 (1993).

Hong et al., "The Interaction of Artemisinin with Malarial Hemozoin," *Mol. Biochem. Parasit.* 63:121–128 (1974).

Stout, D. L., "The Role of Transferrin in Heme Transport," *Biochim. Biophy. Res. Comm.* 189:765–770 (1992).

Smith et al., "Expression of Haemopexin–Transport System in Cultured Mouse Hepatoma Cells," *Biochem. J.* 256:941–950 (1988).

Smith et al., "Hemopexin Joins Transferrin as Representative Members of a Distinct Class of Receptor-Mediated Endocytic Transport Systems," *Europ. J. Cell Biol.* 53:234–245 (1990).

Meshnick et al., "Activated Oxygen Mediates the Antimalarial Activity of Qinghaosu," *Prog. Clin. Biol. Res.* 313:95–104 (1989).

Krungkrai et al., "The Antimalarial Action on *Plasmodium falciparum* of Qinghaosu and Artesunate in Combination with Agents Which Modulate Oxidant Stress," *Tran. Roy. Soc. Trop. Med. Hyg.* 81:710–714 (1989).

Levander et al., "Qinghaosu, Dietary Vitamin E, Selenium, and Cod Liver Oil: Effect on the Susceptibility of Mice to the Malarial Parasite *Plasmodium yoelii*," *Am. J. Clin. Ntr.* 50:346–352 (1989).

Biirgen et al., "Ro. 42–1611, A New Effective Antimalarial: Chemical Structure and Biological Activity," *Sixth International Congress for Infectious Diseases*, Abst. 427, p. 152, Apr. 1994, Prague.

Peters et al., "The Chemotherapy of Rodent Malaria. XLIX. The Activities of Some Synthetic 1,2,4–Trioxanes Against Chloroquinine–Sensitive and Chloroquinine–Resistant Parasites. Part 2: Structure–Activity Studies on cis–fused Cyclopenteno–1,2,4–Trioxane (Fenozans) Against Drug–Sensitive and Drug–Resistant Lines of *Plasmodium berghei* and *P. yoelii* spp. NS In Vivo," *Annals of Tropical Medicine and Parasitology*, 87(1):9–16 (1993).

Vennerstrom et al., "Dispiro–1,2,4,5–tetraoxanes: A New Class of Antimalarial Peroxides," *J. of Medicinal Chemistry* 35(16):3023–3027 (1992).

Vidal et al., "Human T Lymphocyte Virus I Infection Deregulates Surface Expression of the Transferrin Receptors," *J Immunol.* 141:984–988 (1988).

Asawamahasakda, W. et al., "Reaction of Antimalarial Endoperoxides with Specific Parasite Proteins," *Antimicrob. Agents Chemother.* 38:1854–1858 (1994).

Hofheinz, W. et al., "Ro42–1611 (arteflene), a new effective antimalarial: chemical structure and biological activity," *Trop. Med. Parasitol.* 45:261–265 (1994).

*Primary Examiner*—Frederick Krass
*Attorney, Agent, or Firm*—Christensen O'Connor Johnson & Kindness PLLC

[57] ABSTRACT

Methods of inhibiting or killing cancer cells are disclosed wherein compounds having an endoperoxide moiety that is reactive with heme are administered under conditions which enhance intracellular iron concentrations. Representative endoperoxide compounds include endoperoxide bearing sesquiterpene compounds such as artemisinin and its analogs, arteflene and its analogs, 1,2,4-trioxanes and 1,2,4,5-tetraoxanes. Intracellular iron concentrations may be enhanced by the administration of iron salts or complexes.

13 Claims, 2 Drawing Sheets

METHODS OF INHIBITION OR KILLING CANCER CELLS USING AN ENDOPEROXIDE

FIELD OF THE INVENTION

The present invention relates to the inhibition or killing of cancer cells. More particularly, the present invention relates to the systemic and topical treatments of cancer cells with sesquiterpene compounds.

BACKGROUND OF THE INVENTION

Artemisinin (Qinghaosu) and its analogs are the treatments of choice for cerebral or chloroquine resistant malaria or for patients with chloroquine allergy. Artemisinin is a naturally occurring substance, obtained by purification from sweet wormwood, *Artemisia annua* L. Artemisinin and its analogs are sesquiterpene lactones with a peroxide bridge, and are characterized by very low toxicity and poor water solubility. Artemisinin is known as a humoral immunosuppressive agent which is less active than cyclophosphamide, the latter being one of the major chemotherapeutic agents for carcinomas. Artemisinin stimulates cell-mediated immunity, and yet decreases abnormally elevated levels of polyamine regulatory proteins. It also markedly inhibits nucleic acid and protein syntheses. Further, it affects cellular membrane functions and decreases hepatic cytochrome oxidase enzyme system activity. Still further, it is virustatic against influenza and cidal against three groups of pathogenic parasites.

Known analogs of artemisinin which have higher solubility in water are dihydroartemisinin, artemether, artesunate, arteether, propylcarbonate dihydroartemisinin and artelinic acid. Dihydroartemisinin has an antimalarial potency which is 60% higher than that of artemisinin. Artemether and artesunate have antimalarial potencies which are 6 times and 5.2 times, respectively, that of artemisinin. In terms of their ability to inhibit nucleic acid synthesis, dihydroartemisinin, artemether, artesunate, arteether, and propylcarbonate dihydroartemisinin all have 100 times the activity of artemisinin, and protein synthesis is stimulated to an even greater extent by these compounds. Artesunate stimulates the immune system at low doses and inhibits it at high doses. Artelinic acid is the most water-soluble and the most stable of the group. Two of the compounds in this group have been demonstrated to display synergistic activity with doxorubicin (a chemotherapeutic agent) and miconazole (an antifungal agent) in the in vitro killing of *Plasmodium falciparum*, the etiologic agent of malaria.

The very low toxicity of these compounds to humans is a major benefit. Artesunate, for example, is twice as safe as artemether and only one-fiftieth as toxic as chloroquinine, the most common antimalarial. The first manifestation of toxicity of these compounds is generally a decreased reticulocyte count. Other manifestations include transient fever, decreased appetite and elevated blood transaminase levels, the latter an indication of hepatotoxicity.

U.S. Pat. No. 4,978,676 discloses the use of artemisinin and artemisinin analogs in the treatment of skin conditions such as psoriasis, blistering skin diseases, viral warts, and hemorrhoids.

U.S. Pat. No. 4,978,676 discloses the use of combinations artemisinin and artemisinin analogs with monocarboxylic acids, esters or amides in the treatment of papulosquamous skin diseases, including psoriasis, an eczematous skin diseases, including seborrheic and atopic dermatitis.

U.S. Pat. No. 5,219,880 discloses the use of artemisinin and artemisinin analogs in the treatment of warts, molluscum contagiosum and hemorrhoids.

U.S. Pat. No. 5,225,427 discloses certain 10-substituted ether derivatives of dihydroartemisinin alleged to exhibit antimalarial and antiprotozoal activity.

Artemisinin alone has been shown to be toxic to cancer cells in vitro at 20 to 180 μM range (Sun et al., "Antitumor Activities of 4 Derivatives of Artemisic Acid and Artemisinin B in vitro," *Chung-Kuo-Yao-Li-Hsueh-Pao* 13:541–543 (1992)). The effect was found to be more effective for hepatoma and embryonic lung cells than against human gastric cancer cells. In another study (Woerdenbag et al., "Cytotoxicity of Artimisinin-related Endoperoxides to Erlich Ascites Tumor Cells," *J. Nat. Prod.* 56(6):849–856 (1993)), artemisinin was shown to have an $IC_{50}$ value of 29.8 μM on Ehrlich ascites tumor cells. Several derivatives of dihydroartemisinin (artemether, arteether, sodium artesunate, artelinic acid, and sodium artelinate) had $IC_{50}$ values ranged from 12.2 to 19.9 μM. A ether dimer of dihydroartemisinin was found to have an $IC_{50}$ of 1.4 μM. However, the toxicity of the dimer to normal cells was not tested. The authors of the latter paper concluded that, "The artemisinin-related endoperoxides showed cytotoxicity to Ehrlich ascites tumor cells at higher concentrations than those needed for in vitro antimalarial activity, as reported in the literature." However, serum concentrations at the levels reported by the two papers cannot be reached in vivo.

Artemisinin is a relatively safe drug with little side-effects even at high doses. Oral dose of 70 mg/kg/day for 6 days has been used in humans for malaria treatment. Furthermore, more potent analogs of this and similar compounds are also available. Higher efficacy of artemisinin action also can be achieved by other means. For example, artemisinin is more reactive with heme than free iron (Hong, et al. "The Interaction of Artemisinin with Malarial Hemozoin," *Mol. Biochem. Parasit.* 63:121–128 (1974)). Heme can be introduced into cells using transferrin (Stout, D. L., "The Role of Transferrin in Heme Transport," *Biochim. Biophy. Res. Comm.* 189:765–770 (1992)) or the heme-carrying compound hemoplexin (Smith et al., "Expression of Haemopexin-Transport System in Cultured Mouse Hepatoma Cells," *Biochem. J.* 256:941–950 (1988); Smith et al., "Hemopexin Joins Transferrin as Representative Members of a Distinct Class of Receptor-Mediated Endocytic Transport System," *Europ. J. Cell Biol.* 53:234–245 (1990)). The effectiveness of artemisinin also can be enhanced by increasing oxygen tension, decreasing intake of antioxidants, and blockade of peroxidase and catalase by drugs such as miconazole (Meshnick et al., "Activated Oxygen Mediates the Antimalarial Activity of Qinghaosu," *Prog. Clin. Biol. Res.* 313:95–104 (1989); Krungkrai et al., "The Antimalarial Action on *Plasmodium falciparum* of Qinghaosu and Artesunate in Combination with Agents Which Modulate Oxidant Stress," *Tran. Roy. Soc. Trop. Med. Hyg.* 81:710–714 (1989); Levander et al., "Qinghaosu, Dietary Vitamin E, Selenium, and Cod Liver Oil: Effect on the Susceptibility of Mice to the Malarial Parasite *Plasmodium yoelii*," *Am. J. Clin. Ntr.* 50:346–352 (1989)).

The endoperoxide moiety of artemisinin and its analogs has been found to be necessary for antimalarial activity, and analogs lacking this group have been found to be inactive. In the presence of heme, the endoperoxide bridge undergoes reductive decomposition to form a free radical and electrophilic intermediates. Accordingly, endoperoxide bearing compounds other than artemisinin and its analogs have been found to have antimalarial activity. For example, arteflene (Ro. 42–1611; Biirgen et al., "Ro. 42–1611, A New Effective Antimalarial: Chemical Structure and Biological Activity," *Sixth International Congress for Infectious Diseases*, Abst. 427, p. 152, April 1994, Prague), and the 1,2,4-trioxanes, such as the fenozans (Peters et al., "The Chemotherapy of Rodent Malaria. XLIX. The Activities of Some Synthetic 1,2,4-Trioxanes Against Chloroquinine-Sensitive and Chloroquinine-Resistant Parasites. Part 2: Structure-Activity Studies on cis-fused Cyclopenteno-1,2,4-Trioxane (Fenozans) Against Drug-Sensitive and Drug-Resistant Lines of *Plasmodium berghei* and *P. yoelii* spp. NS In Vivo," *Annals of Tropical Medicine and Parasitology*, 87(1):9–16 (1993)), and the 1,2,4,5-tetraoxanes (Vennerstrom et al., "Dispiro-1, 2,4,5-tetraoxanes: A New Class of Antimalarial Peroxides," *J. of Medicinal Chemistry*, 35( 16):3023–3027 (1992)).

SUMMARY OF THE INVENTION

It has been discovered that the anticancer activity of compounds having an endoperoxide moiety that is reactive with heme and iron, of which artemisinin and its analogs, arteflene and its analogs, 1,2,4-trioxanes and 1,2,4,5-tetraoxanes are representative examples, is substantially enhanced both in vitro and in vivo when administered under conditions which enhance intracellular iron concentrations.

In one embodiment of the invention, the endoperoxide bearing compounds have a sesquiterpene structure, particularly an oxygenated tricyclic sesquiterpene structure with an endoperoxide group, and preferably those which are sesquiterpene lactones or alcohols, carbonates, esters, ethers and sulfonates thereof. Examples of such compounds include artemisinin; dihydroartemisinin; carbonate, sulfonate, ester and ether derivatives of dihydroartemisinin, notably artemether, arteether, artesunate and artesunate salts, and dihydroartemisinin propyl carbonate; and the bis-ether artelinic acid.

Iron agents useful for enhancing intracellular iron concentrations in connection with the practice of the invention include pharmaceutically acceptable iron salts and iron complexes.

In addition to the sesquiterpene compounds and the iron enhancing agents, compositions of the present invention may further comprise the administration of conventionally used antineoplastic agents, such as androgen inhibitors, antiestrogens, cytotoxic agents, hormones, nitrogen mustard derivatives, steroids and the like, as a means of further enhancing clinical efficacy.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
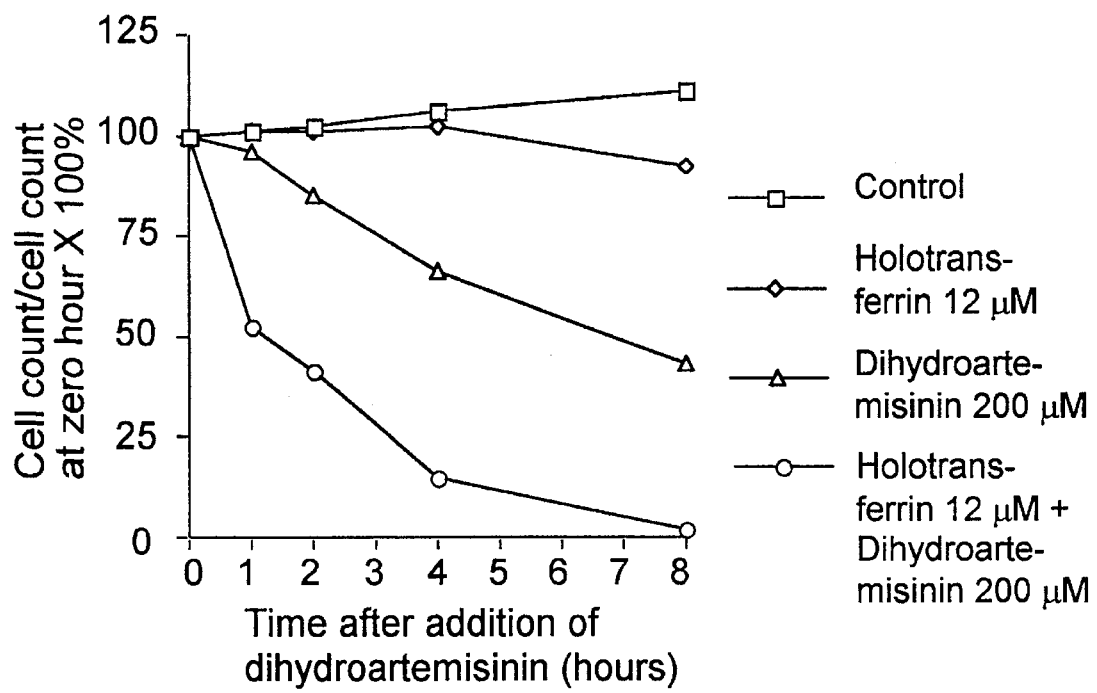
FIG. 1 is a time response curve of molt-4 human leukemia cells incubated in holotransferrin (12 µM) and dihydroartemisinin (200 µM), as described in Example 1. Dihydroartemisinin was added at time zero, one hour after the addition of holotransferrin. Each response curve is the average from four experiments.

In accordance with the present invention, it has been discovered that the ability to kill cancer cells of compounds having an endoperoxide moiety that is reactive with heme and iron, particularly artemisinin and artemisinin analogs, arteflene and its analogs, 1,2,4-trioxanes and 1,2,4,5-tetraoxanes, can be significantly enhanced by increasing the iron concentration in the body of a patient, such as by the administration of iron salts or complexes, followed by administration of the endoperoxide compound. Analogs of artemisinin, in general molecules containing sesquiterpene lactone with a peroxide, arteflene and its analogs, 1,2,4-trioxanes and 1,2,4,5-tetraoxanes are particularly preferred for this purpose. Both iron salts or complexes and the endoperoxide compound can be administered orally. It is presently particularly preferred that iron salt or complex be administered before the endoperoxide compounds such that cancer cells will be preloaded with iron to induce free radical formation with the endoperoxide compound.

Transferrin is an endogenous protein which transports iron and heme from the circulation into cells. Transferrin binds to transferrin receptors on cell surface, and via endocytosis is taken inside the cell and iron is then released. Most cancer cells express higher cell surface concentration of transferrin receptors than normal cells and have high rates of iron influx via transferrin receptors, because iron is needed in cell growth and division. For example, human hepatoma cells can express 800,000 transferrin receptors per cell on the cell surface, whereas normal lymphocytes generally express no transferrin receptors. The entire population of transferrin receptors on a mouse teratocarcinoma stem cell can be internalized within 6 min.

An artemisinin molecule, as a representative endoperoxide compound of the invention, is a sesquiterpene lactone containing an endoperoxide bridge that can be catalyzed by iron to form free radicals. Its antimalarial action is due to its reaction with the iron in free heme molecules in malaria parasite with the generation of free radicals leading to cellular destruction. The present invention takes advantage of this property of artemisinin and targets it towards cancer cells. This selectivity in action is because cancer cells have higher concentration of transferrin receptors on their cell membrane and pick up iron at a higher rate than normal cells. In the presence of artemisinin, increase in iron concentration inside cancer cells will lead to free radical formation intracellularly and cell death.

In accordance with the present invention, a human or animal patient is treated by enhancing the iron concentration in extracellular fluids in the patient and administering to the patient a compound comprising an endoperoxide group that is reactive with heme or iron.

In connection with the present invention, compounds may be employed, in general, that possess an endoperoxide group that reacts in the presence of heme to form free radicals.

Representative, presently preferred endoperoxide compounds are set forth herein, although it will be apparent that other endoperoxide compounds will be useful for this purpose.

Preferred endoperoxide bearing sesquiterpene compounds of the present comprise compounds of the formula:

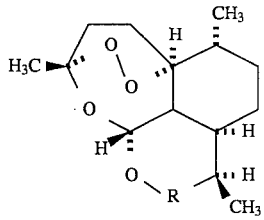

wherein R is

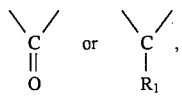

where $R_1$ is hydrogen, hydroxyl, alkyl, or has the formula:

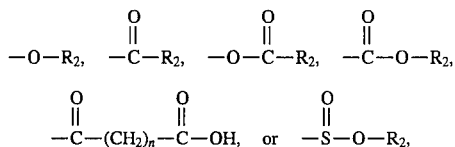

wherein $R_2$ is alkyl or aryl and n is 1 to 6, and the pharmaceutically acceptable salts thereof. As used herein, the term "alkyl" means lower alkyl having from 1 to 6 carbon atoms, preferably 1 to 4 carbon atoms. Alkyl groups of the invention may be straight-chain or branched-chain groups, with straight-chain groups preferred. The term "aryl" preferably refers to phenyl and benzyl, with phenyl the most preferred. Pharmaceutically acceptable salts include the alkali or alkaline earth metal salts, preferably sodium or potassium, with sodium the most preferred.

The presently particularly preferred sesquiterpene compounds of the invention include artemisinin, where R is

dihydroartemisinin ($R_1$=—OH), artesunic acid ($R_1$=—OCO(CH$_2$)$_2$CO$_2$H), and artesunate, artemether ($R_1$=—OCH$_3$) and arteether ($R_1$=—OC$_2$H$_5$). The presently most particularly preferred sesquiterpene compound of the invention is dihydroartemisinin.

Other representative endoperoxide compounds of the invention include arteflene (Ro. 42-1611) and its analogs (Biirgen et al., supra), 1,2,4-trioxanes (Peters et al., supra) and 1,2,4,5-tetraoxanes (Vennerstrom et al., supra).

Preferred agents for enhancing intracellular iron levels for use in combination with the sesquiterpenes of the present invention include pharmaceutically acceptable iron salts and iron complexes. Iron salts useful in the practice of the invention include ferrous fumarate, ferrous sulfate, ferrous carbonate, ferrous citrate, ferrous gluconate and ferrous lactate. Iron complexes useful in the practice of the invention generally include pharmaceutically acceptable complexes comprising iron, such as, for example, ferrocholinate, ferroglycine sulfate, dextran iron complex, peptonized iron, iron sorbitex, ferric oxide and saccharated iron, as well as iron complexed with iron binding proteins and glycoproteins, such as the holoferritins and holotransferrins.

The concentrations of the endoperoxide compounds in the formulations to be applied in the practice of the present invention will generally range up to the maximally tolerated dosage, but the concentrations are not critical and may vary widely. For artemisinin and its analogs, however, best results will be obtained using formulations containing the compounds at levels of from about 0.1 to about 100 mg per kilogram of body weight per day, preferably from about 1 to about 90 mg per kilogram of body weight per day, and most preferably from about 1 to about 75 mg per kilogram of body weight per day. The precise amounts employed by the attending physician will vary, of course, depending on the compound, route of administration, physical condition of the patent and other factors. The daily dosage may be administered as a single dosage or may be divided into multiple doses for administration. The amount of the compound actually administered for treatment will be a therapeutically effective amount, which term is used herein to denote the amount needed to produce a substantial clinical improvement. Optimal amounts will vary with the method of administration, and will generally be in accordance with the amounts of conventional medicaments administered in the same or a similar form. Topical or oral administration, for instance, may typically be done from once to three times a day.

The concentrations of agents for enhancing intracellular iron concentrations in the practice of the present invention will generally range up to the maximally tolerated dose for a particular subject and agent, which will vary depending on the agent, subject, disease condition and other factors. Dosages ranging from about 1 to about 100 mg of iron per kilogram of subject body weight per day will generally be useful for this purpose.

This procedure will be most effective for the treatment of aggressive cancer, in which large number of transferrin receptors are expressed on the cell surface. However, the procedure may not be effective in the treatment of certain types of cancer. For example, some adult T-cell leukemia have defective internalization of transferrin receptors and may not be susceptible to this treatment. (Vidal et al., "Human T Lymphocyte Virus I Infection Deregulates Surface Expression of the Transferrin Receptors," *J. Immunol.* 141:984–988 (1988)) Furthermore, this procedure can be used in prophylactic cancer prevention, prevention of cancer recurrence and metastases after surgery, and as an adjuvant of other traditional cancer therapy.

More potent and water soluble analogs of artemisinin and similar compounds, e.g., dihydroartemisinin, artesunate, artether, and artemether, etc., are available. Higher efficacy of artemisinin action also can be achieved by other means. For example, artemisinin is more reactive with heme than free iron. Heme can be introduced into cells using transferrin or the heme-carrying compound hemoplexin. The effectiveness of artemisinin also can be enhanced by increasing oxygen tension, decreasing intake of antioxidants, and blockade of peroxidase and catalase by drugs such as miconazole.

The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

The optimal systemic formulation of the basic combination of the present invention, i.e., the combination of sesquiterpene lactone with an intracellular iron enhancing agent, may vary from one such combination to the next.

The formulations of the present invention may further include as optional ingredients one or more agents already known for their use in the inhibition of cancer cells, for added clinical efficacy. Such combinations will in some cases provide added benefit. These agents include, for example, androgen inhibitors, such as flutamide and luprolide, antiestrogens, such as tomoxifen, antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin and idamycin, hormones, such as medroxyprogesterone, estramustine, ethinyl estradiol, estradiol, leuprolide, megestrol, octreotide, diethylstilbestrol, chlorotrianisene, etoposide, podophyllotoxin and goserelin, nitrogen mustard derivatives, such as melphalan, chlorambucil, methlorethamine and thiotepa, steroids, such as betamethasone, and other antineoplastic agents, such as live *Mycobacterium bovis*, dicarbazine, asparaginase, leucovorin, mitotane, vincristine, vinblastine and taxotere. Appropriate amounts in each case will vary with the particular agent, and will be either readily known to those skilled in the art or readily determinable by routine experimentation.

The endoperoxide compounds and iron agents of the invention may be employed in vitro, in vivo or ex vivo for killing of target cancer cells. For in vivo applications, compositions of the endoperoxide compounds of the invention generally comprise an amount of the endoperoxide compounds effective, when administered to a human or other animal subject, to localize a sufficient amount of the endoperoxide compounds at target tissue sites to facilitate target cell killing, together with a pharmaceutically acceptable carrier. Any pharmaceutically acceptable carrier may be generally used for this purpose, provided that the carrier does not significantly interfere with the stability or bioavailability of the sesquiterpene compounds of the invention.

The compositions of the invention can be administered in any effective pharmaceutically acceptable form to warm blooded animals, including human and other animal subjects, e.g., in topical, lavage, oral, suppository, parenteral, or infusable dosage forms, as a topical, buccal, or nasal spray or in any other manner effective to deliver the agents to a site of target cells. The route of administration will preferably be designed to optimize delivery and localization of the agents to the target cells.

For topical applications, the pharmaceutically acceptable carrier may take the form of liquids, creams, lotions, or gels, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Compositions designed for injection may comprise pharmaceutically acceptable sterile aqueous or nonaqueous solutions, suspensions or emulsions. Examples of suitable nonaqueous carriers, diluents, solvents, or vehicles include propylene glycol, polyethylene glycol, vegetable oils, such as olive oil, and injectable organic esters such as ethyl oleate. Such compositions may also comprise adjuvants such as preserving, wetting, emulsifying, and dispensing agents. They may be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

Solid dosage forms for oral or topical administration include capsules, tablets, pills, suppositories, powders, and granules. In solid dosage forms, the compositions may be admixed with at least one inert diluent such as sucrose, lactose, or starch, and may additionally comprise lubricating agents, buffering agents, enteric coatings, and other components well known to those skilled in the art.

Actual dosage levels of the compositions of the invention may be varied so as to obtain amounts of the sesquiterpene compound and iron at the site of target cells, especially tumor cells, effective to obtain the desired therapeutic or prophylactic or diagnostic response. Accordingly, the selected dosage level will depend on the nature and site of the target cells, the desired quantity of sesquiterpene compound and iron required at the target cells for target cell inhibition or killing purposes, the nature of the sesquiterpene compound and iron agent employed, the route of administration, and other factors. Generally, for oral delivery routes of administration, effective administration doses will include from about 1 to about 100 mg/kg of iron containing agent, more preferably from about 10 to about 90 mg/kg of iron containing agent per kilogram of body weight of the subject per day, and from about 0.1 to about 100 mg/kg of an endoperoxide compound of the invention, more preferably from about 1 to about 90 mg/kg of the endoperoxide compound per kilogram of body weight of the subject per day. The foregoing doses may be administered as a single dose or may be divided into multiple doses for administration, e.g., up to three times per day.

EXAMPLES

EXAMPLE 1

In Vitro Cancer Cell Inhibition

Molt-4-lymphoblastoid cells and human lymphocytes were used in the experiment. Molt-4-lymph cells were purchased from the American Type Culture Collection (Rockville, Md.). They are acute lympoblastic leukemia cells from human peripheral blood. Cultures were maintained in RPMI-1640 (Gibco, Long Island, N.Y.) supplemented with 10% fetal bovine serum (Hyclone, New Haven, Conn.). Cells were cultured at 37° C. in 5% $CO_2$/95% air and 100% humidity, and were split 1:2 at a concentration of approximately $1\times10^6$/ml. Approximate cell number before experiment were between $150\times10^3$ to $300\times10^3$ per ml. Human lymphocytes were isolated from fresh blood obtained from a healthy donor and isolated using a modification of the Ficoll-hypaque centrifugation method of Boyum, A., "Isolation of Mononuclear Cells and Granulocytes from Human Blood," *Scand. Clin. Lab. Invest.* 21:77–89 (1968). In this method, 20–100 μl of whole blood obtained from a finger prick was mixed with 0.5 ml of ice-cold RPMI-1640 without phenol red (GIBCO, N.Y.) in a 1.5 ml heparinized microfuge tube (Kew Scientific Inc., Columbus, Ohio). Using a Pipetman, 100 μl of cold lymphocyte separation medium (LSM) was layered at the bottom of the tube. The samples were centrifuged at 3500 rpm for 2 min in a microfuge (Sorvall, Microspin model 245) at room temperature. The lymphocytes in the upper portion of the Ficoll layer were pipetted out. Cells were washed twice in 0.5 ml RPMI-1640 by centrifugation for 2 min at 3500 rpm in the microfuge. The final pellet consisting of approximately $0.4–2.0 \times 10^5$ lymphocytes was resuspended in RPMI-1640. Cell viability was determined before experiments using trypan blue exclusion and found to be more than 95%.

Cells (Molt-4 and lymphocytes) were aliquoted in 0.1 ml volumes into microfuge tubes. Human holotransferrin (Sigma Chemicals, St. Louis, Mo.) was added to samples of the cells. Different concentrations of freshly prepared dihydroartemisinin dissolved in complete medium were added 1 hr later to the tubes. The final concentration of holotransferrin was 12 μM and dihydroartemisinin was either 1, 10, 50, or 200 μM. Equal volume of medium was added to control samples (i.e., samples without holotransferrin nor dihydroartemisinin). Cells were kept in an incubator at 37° C. under 5% $CO_2$ and 95% air during the experiment. At 1, 2, 4, and 8 hrs after the addition of dihydroartemisinin, the cell number was counted from a 10 μl aliquot from the samples using a hemocytometer. The cells were thoroughly mixed by repeated pipeting before an aliquot was taken for counting. In the case of Molt-4 cells, cell viability was not determined because it is not correlated with cell loss as rapid cell disintegration was observed.

Figure 2:
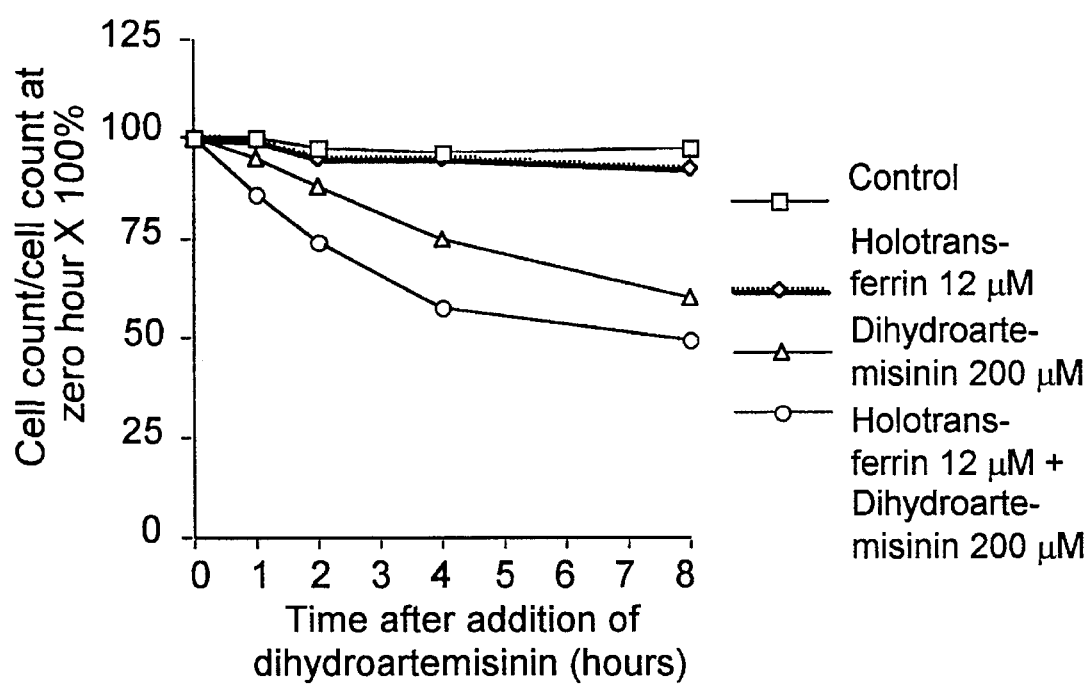
FIG. 2 is a time response curve of normal human lymphocytes incubated in holotransferrin (12µM) and dihydroartemisinin (200 µM), as described in Example 1. Dihydroartemisinin was added at time zero, one hour after the addition of holotransferrin. Each response curve is the average from four experiments.

Data are expressed as percentage of cell count at a certain time point compared to cell count at the time when dihydroartemisinin was added (time zero in FIGS. 1 and 2). Time-response curves were compared by the method of Krauth, J., "Nonparametric Analysis of Response Curves," *J. Neurosci. Method* 2:239–252 (1980). The level of the curves, i.e., $a_o$ of the orthogonal polynomial coefficient, were compared with the median test. $\chi^2$ was calculated with Yates's correction for continuity. The difference between two data points was also compared by the median test. A difference at $p<0.05$ was considered statistically significant. The Probit analysis was used to determine $LD_{50}$s, i.e., the concentration of dihydroartemisinin that causes a decrease in cell count by 50% in 8 hrs, from the dose-response data.

The percent cell count at different times after the addition of 200 μM of dihydroartemisinin of Molt-4 cells and lymphocytes are shown in FIGS. 1 and 2, respectively. In both Molt-4 and lymphocytes, no significant difference in cell counts was observed between control samples and samples exposed to holotransferrin (12 μM) alone ($\chi^2=0.5$, df=1, non-significant) during the 8-hr incubation period. Compared to controls, a significant decrease in cell count (FIG. 1) was observed in Molt-4 cells exposed to dihydroartemisinin alone ($\chi^2=4.5$, df=1, p<0.035 compared to control), and a combination of dihydroartemisinin and holotransferrin ($\chi^2=4.5$, df=1, p<0.035 compared to control). In addition, percent cell counts of the combined drug treatment were significantly less than those treated with dihydroartemisinin alone ($\chi^2=4.5$, df=1, p<0.035 compared to control).

In the case of lymphocytes, exposure to dihydroartemisinin alone or dihydroartemisinin plus holotransferrin, cell counts were significantly less than those of the controls ($\chi^2=4.5$, df=1, p<0.035 compared to control). However, the addition of holotransferrin did not significantly further enhance the effect of dihydroartemisinin alone ($\chi^2=0.5$, df=1, no significant difference between the dihydroartemisinin alone and holotransferrin+dihydroartemisinin response curves).

Figure 3A:
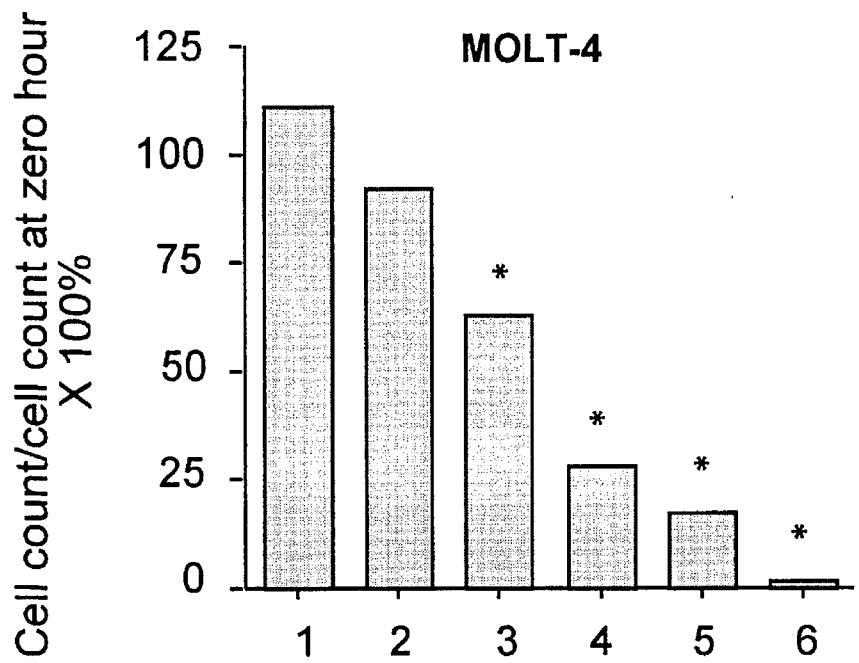
FIG. 3 is a dose-response relationship of molt-4 cells (FIG. 3A) and lymphocytes (FIG. 3B) exposed to holotransferrin and dihydroartemisinin. Treatment 1 is control samples with no drug added. Samples in treatments 2–6 contained 0, 1, 10, 50, and 200 µM of dihydroartemisinin, respectively, plus 12 µM of holotransferrin. Holotransferrin was added at 1 hr before the addition of dihydroartemisinin. Cell counts were done at 8 hours after addition of dihydroartemisinin. Each bar represents the average from four experiments.
Figure 3B:
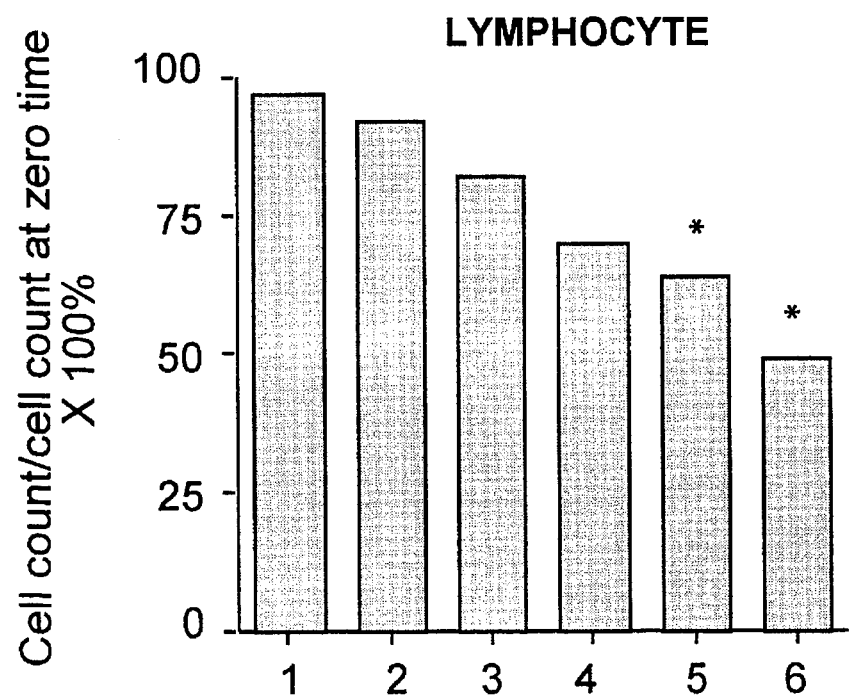

FIGS. 3A and 3B show the dose-response relationship of dihydroartemisinin for Molt-4 and lymphocytes, respectively, incubated in 12 μM of holotransferrin. The percent cell counts from samples at 8 hrs after addition of various concentrations of dihydrotransferrin is presented. Dose-dependent decreases in cell counts were observed. For Molt-4 cells, a significant difference (from control samples, $\chi^2=4.5$, df=1, p<0.035) was observed at 1 μM of dihydroartemisinin and higher. Smaller decreases in cell counts were observed with lymphocytes under similar treatment conditions. A significant difference from control samples was observed only at a concentration of dihydroartemisinin of 50 μM and higher. Probit analysis of the data showed that the $LD_{50}$s for Molt-4 cells and lymphocytes were 2.59 and 230 μM, respectively.

The foregoing results demonstrate that combined incubation in holotransferrin and dihydroartemisinin can selectively destroy human cancer cells, whereas the effect is significantly less on normal lymphocytes. Artemisinin alone has been shown to be toxic to cancer cells in vitro at 20 to 180 μM range (Sun et al., supra). The effect was found to be more effective for hepatoma and embryonic lung cells than against human gastric cancer cells. However, serum concentrations at these levels cannot be reached in vivo. Addition of holotransferrin increases the potency and selectivity of the drug and may decrease the time of cell killing. In the combined treatment, considerable cell death was observed at a concentration of dihydroartemisinin of 1 μM after 8 hrs of incubation. Furthermore, there is reason to believe that artemisinin can work at lower concentrations in vivo than in vitro. Culture medium may contain 19–30 μM of free iron and could cause destruction of dihydroartemisinin molecules before they can gain entry into cells.

EXAMPLE 2

In Vivo Dog Study 1

A 7 year old male canine basset hound was diagnosed with lymphosarcoma of the lymph nodes. Artemisinin (10 mg per day, i.v., approx. 0.3 mg/kg) and ferrous sulfate (10 mg per day, p.o.) was given in three settings of five days each, with an interval between each treatment period of three to five days. The ferrous sulfate was administered six hours before artemisinin administration. The diameter size of inguinal and submandibular, right and left lymph nodes was reduced to half within five days of treatment. A reduction in size was observed in prescapular and popliteal lymph nodes. The diameter of all lymph nodes increased within two weeks of cessation of therapy. The dog survived for five months after treatment and then was euthanised.

EXAMPLE 3

In Vivo Dog Study 2

A female canine retriever was operated on for hemangiopericytoma of the right thigh. One week after the operation, artemisinin (10 mg per day, p.o.) plus ferrous sulfate (10 mg per day, p.o.) therapy was initiated and continued for 23 consecutive days. As in Example 2, iron sulfate was given six hours before artemisinin each day. No signs of tumor recurrence were seen during or at three months after therapy period.

EXAMPLE 4

In Vivo Dog Study 3

A 12 years old, female canine was diagnosed with a malignant mast cell tumor, grade 11, on the right thoracic wall. The dog underwent surgery, and was treated with ferrous sulfate (10 mg per day, p.o.) and artemisinin (10 mg per day, p.o. ) for seven days and then on artemisinin alone (10 mg per day, p.o.) for the next ten days. Examination after four weeks of therapy, showed no signs of tumor recurrence. The canine owner reported no sign of recurrence at four months after treatment.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for the treatment of a human or non-human mammal patient suffering from cancer, said method comprising identifying a patient in need of such treatment and then:
   (a) administering to said patient an amount of an iron enhancing agent effective to increase the intracellular iron concentration of the patient; and
   (b) administering to said patient a therapeutically effective amount of a compound containing an endoperoxide group wherein the endoperoxide compound is selected from the group consisting of sesquiterpene lactones and alcohols, carbonates, esters, ethers and sulfonates thereof, arteflene, 1,2,4-trioxanes and 1,2,4,5-tetraoxanes.

2. A method in accordance with claim 1 in which the endoperoxide compound is a member selected from the group consisting of sesquiterpene lactones and alcohols, carbonates, esters, ethers and sulfonates thereof.

3. A method in accordance with claim 1 in which the endoperoxide compound is a compound of the formula:

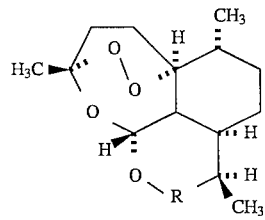

wherein R is

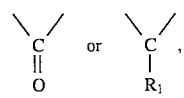

where $R_1$ is hydrogen, hydroxyl, alkyl, or has the formula:

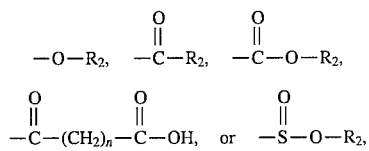

wherein $R_2$ is alkyl or aryl and n is 1 to 6, or a pharmaceutically acceptable salt thereof.

4. A method in accordance with claim 1 in which the endoperoxide compound is a sesquiterpene compound selected from the group consisting of artemisinin, dihydroartemisinin, artemether, arteether, artesunate, artelinic acid and dihydroartemisinin propyl carbonate.

5. A method in accordance with claim 4 in which the sesquiterpene compound is dihydroartemisinin.

6. The method of claim 1 wherein the endoperoxide compound is arteflene.

7. The method of claim 1 wherein the endoperoxide is a 1,2,4-trioxane.

8. The method of claim 1 wherein the endoperoxide is a 1,2,4,5-tetraoxane.

9. A method in accordance with claim 1 in which the iron enhancing agent is selected from the group consisting of ferrocholinate, ferroglycine sulfate, dextran iron complex, peptonized iron, iron sorbitex, ferric oxide, saccharated iron, holoferritins and holotransferrins.

10. A method of claim 1 wherein the iron enhancing agent is administered to the patient prior to administering the endoperoxide compound.

11. A method in accordance with claim 2 comprising administering to said patient from about 0.1 to about 100 mg of the sesquiterpene compound per kilogram of body weight of the patient per day, and from about 1 to about 100 mg of iron per kilogram of body weight of the patient per day.

12. A method in accordance with claim 1 which further comprises administering to the patient an antineoplastic agent selected from the group consisting of androgen inhibitors, antiestrogene, cytotoxic agents, hormones, nitrogen mustard derivatives and steroids.

13. A method in accordance with claim 1 comprising administering said endoperoxide compound topically or systemically by oral, intramuscular or intravenous administration.

* * * * *